US011241369B2

(12) United States Patent
Chen et al.

(10) Patent No.: US 11,241,369 B2
(45) Date of Patent: Feb. 8, 2022

(54) SKIN-BRIGHTENING COMPOSITIONS AND METHODS

(71) Applicant: L'OREAL, Paris (FR)

(72) Inventors: Rebecca Chen, Princeton, NJ (US); Anne-Laure Suzanne Bernard, New York, NY (US); Mickael Ange Agach, Saint-Ouen (FR); Leila Safia Camille Hercouet, Neuilly Plaisance (FR); Etienne Huguet, Antony (FR)

(73) Assignee: L'OREAL, Paris (FR)

( * ) Notice: Subject to any disclaimer, the term of this patent is extended or adjusted under 35 U.S.C. 154(b) by 441 days.

(21) Appl. No.: 15/827,726

(22) Filed: Nov. 30, 2017

(65) Prior Publication Data

US 2019/0159980 A1    May 30, 2019

(51) Int. Cl.
*A61K 8/19* (2006.01)
*A61K 8/22* (2006.01)
*A61K 8/31* (2006.01)
*A61K 8/41* (2006.01)
*A61K 8/43* (2006.01)
*A61K 8/44* (2006.01)
*A61K 8/368* (2006.01)
*A61Q 19/02* (2006.01)

(52) U.S. Cl.
CPC .................. *A61K 8/19* (2013.01); *A61K 8/22* (2013.01); *A61K 8/31* (2013.01); *A61K 8/368* (2013.01); *A61K 8/41* (2013.01); *A61K 8/43* (2013.01); *A61K 8/44* (2013.01); *A61Q 19/02* (2013.01); *A61K 2800/30* (2013.01); *A61K 2800/524* (2013.01); *A61K 2800/882* (2013.01)

(58) Field of Classification Search
None
See application file for complete search history.

(56) References Cited

U.S. PATENT DOCUMENTS

| 6,325,783 | B1 | 12/2001 | Laughlin et al. |
| 7,740,663 | B2 | 6/2010 | De La Mettrie et al. |
| 7,927,381 | B2 * | 4/2011 | Hercouet ................. A61K 8/86 8/405 |
| 7,988,738 | B2 * | 8/2011 | Hercouet ................. A61K 8/06 132/202 |
| 8,262,739 | B2 * | 9/2012 | Hercouet ................ A61K 8/062 8/101 |
| 8,556,992 | B2 | 10/2013 | DeGeorge et al. |
| 9,017,424 | B2 * | 4/2015 | Hercouet ................. A61K 8/31 8/404 |
| 2006/0117494 | A1 | 6/2006 | Marsh |
| 2006/0121100 | A1 | 6/2006 | Opremcak |
| 2006/0161121 | A1 | 7/2006 | Klaveness |
| 2007/0166339 | A1 | 7/2007 | Gupta |
| 2007/0186357 | A1 | 8/2007 | Chalmers et al. |
| 2008/0193393 | A1 | 8/2008 | Dayan |
| 2009/0162309 | A1 | 6/2009 | Hercouet et al. |
| 2010/0166688 | A1 | 7/2010 | Hercouet et al. |
| 2010/0281627 | A1 | 11/2010 | Matsunaga et al. |
| 2013/0022565 | A1 | 1/2013 | Braida-ValeRio et al. |
| 2016/0158123 | A1 | 6/2016 | Agarwal et al. |

FOREIGN PATENT DOCUMENTS

| FR | 2925298 | A1 | 6/2009 | |
| FR | 2925308 | A1 | 6/2009 | |
| FR | 2974504 | A1 | 11/2012 | |
| FR | 2979233 | A1 | 3/2013 | |
| FR | 2984731 | A1 | 6/2013 | |
| FR | 3007278 | A1 | 12/2014 | |
| FR | 3012332 | A1 | 5/2015 | |
| FR | 3013590 | A1 * | 5/2015 | ............... A61K 8/41 |
| WO | 199960993 | A1 | 12/1999 | |
| WO | 2004069220 | A1 | 8/2004 | |
| WO | WO-2006066640 | A1 * | 6/2006 | ............. A45D 19/02 |
| WO | 2010070243 | A1 | 6/2010 | |
| WO | WO-2014170239 | A1 * | 10/2014 | |
| WO | 2014202779 | A1 | 12/2014 | |
| WO | 2015007916 | A1 | 1/2015 | |

OTHER PUBLICATIONS

Article "Scleroglucan", published by MDPI obtained via www.ncbi. nlm.nih.gov (Year: 2009).*
U.S. Appl. No. 15/855,108, filed Dec. 27, 2017, Chen, Rebecca.
International Search Report for PCT/US2018/062163 dated Feb. 12, 2019.

* cited by examiner

*Primary Examiner* — Alton N Pryor
(74) *Attorney, Agent, or Firm* — McNees Wallace & Nurick LLC

(57) ABSTRACT

A cosmetic composition for brightening skin and a method for brightening skin using the cosmetic composition are provided. The cosmetic composition is ammonia-free and persulfate-free, and includes hydrogen peroxide, at least one alkaline booster and at least one fatty compound present from about at least 30% by weight, based upon the total weight of the composition. The method for brightening skin includes applying to the skin a composition provided as a multi-part system, the parts separately containing two or more sub-compositions each of which comprises one of the hydrogen peroxide and the alkaline booster, one or both comprising a fatty compound component, the sub-combinations combinable at the time of use.

28 Claims, No Drawings

SKIN-BRIGHTENING COMPOSITIONS AND METHODS

FIELD OF THE INVENTION

The present invention is generally directed to a cosmetic composition for brightening skin and a method for brightening skin using the cosmetic composition. More particularly, the present invention is directed to a cosmetic composition for brightening skin comprising hydrogen peroxide, at least one ammonia-free and persulfate-free alkaline booster and at least one fatty compound present from about at least 30% by weight, based upon the total weight of the composition, and a method for brightening skin using the cosmetic composition. The composition is characterized as ammonia-free and persulfate-free.

BACKGROUND OF THE INVENTION

A variety of skin compositions are known that can provide skin brightening benefits. Typically, such products employ oxidizing agents to achieve brightening, and include alkaline boosters to activate the oxidizing agents. One of the difficulties encountered when composing skin-brightening compositions arises because the compositions include alkaline boosters and most commonly used alkaline boosters include aqueous ammonia and/or persulfate. Aqueous ammonia is believed to allow the pH of the composition to be adjusted to an alkaline pH to enable activation of the oxidizing agent and is important to the efficacy by swelling keratinous surface. Ammonia and persulfate based alkaline boosters are known to be strong smelling and generally disagreeable to most consumers both in terms of smell as well as skin sensitivity. And the volatility of the ammonia and persulfate based alkaline boosters typically requires that the amount of booster needed must take into account the amount that will be lost due to volatilization.

It is an object of the present invention to provide a skin care composition that overcomes at least one of the aforementioned drawbacks associated with products that employ ammonia and persulfate based boosters and provides good skin-brightening efficacy. Yet another object of the present invention is to demonstrate a progressive increase in skin-brightening efficacy when applied regularly.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

The compositions and methods hereof are characterized, in various embodiments, as comprising hydrogen peroxide, alkaline boosters, and fatty compound, wherein the composition excludes ammonia and persulfates derivatives, includes fatty compounds at a range from at least about 30% by weight, and impart on the skin a lightning and skin smoothing effect to provide a glowing that is not obtained using compositions that comprise ammonia and persulfate derivatives.

In an exemplary embodiment, a skin-brightening cosmetic composition includes hydrogen peroxide, at least one ammonia-free and persulfate-free alkaline booster with optional catalysts, and at least one fatty compound present in an amount of about 30% or more, by weight, based on the weight of the composition. The composition demonstrates efficiency in whitening that is at least the same as with ammonia containing compositions.

In some particular embodiments, a skin-brightening cosmetic composition includes from about 1 to about 4 wt % of hydrogen peroxide; from about 1 to about 5 wt % of at least one ammonia-free and persulfate-free alkaline booster; and from about 50 to about 60 wt % of at least one fatty compound. In some embodiments the ammonia-free and persulfate-free alkaline booster is selected from the group consisting of guanidine carbonate, arginine, monoethanolamine, triethanolamine, potassium hydroxide, sodium bicarbonate and combinations thereof. In some embodiments the optional catalyst is manganese dioxide. In some embodiments, the fatty compound is selected from the group consisting of mineral oil, hemisqualane, dimethicone, squalane and combinations thereof. The composition is provided as a multi-part system, the parts separately including at least one sub-compositions, a first sub-composition comprising hydrogen peroxide and a second sub-composition comprising the at least one alkaline booster, wherein the least a fatty compound component is provided as one or more of a component of one of the first and second sub-compositions and in a third sub-composition, wherein the sub-compositions are combinable at the time of use, wherein the hydrogen peroxide and the alkaline booster containing sub-compositions are combinable at the time of use. The composition demonstrates efficiency in whitening that is at least the same as with ammonia containing compositions.

In another exemplary embodiment, a skin-brightening cosmetic composition includes hydrogen peroxide, at least one ammonia-free and persulfate-free alkaline booster, at least one fatty compound present in an amount of about 30% or more, by weight, based on the weight of the composition, and one or more of surfactants, polymers, chelating agents and vitamins. In some particular embodiments, the at least one surfactant is present in an amount from about 0.5 to about 4%. In some embodiments, the surfactant is selected from the group consisting of nonionic and anionic surfactants and combinations thereof. The composition demonstrates efficiency in whitening that is at least the same as with ammonia containing compositions.

In another exemplary embodiment, an article of manufacture includes separately packaged sub compositions comprising at least one package containing hydrogen peroxide and at least one package containing an alkaline booster, the packages being provided for mixing prior to application to keratinous tissue. In some alternate embodiments, the article of manufacture may be selected from a tube system with option of a mixing feature, and a pump system or a mixing head.

In another exemplary embodiment, a method for brightening skin includes applying to the skin a composition comprising hydrogen peroxide, at least one ammonia-free and persulfate-free alkaline booster, and at least one fatty compound present in an amount of about 30% or more, by weight, based on the weight of the composition. In some embodiments, the total oil content is about 50% or more. In some examples, the oil phase includes a combination of two or more oils. In some examples, the combinations of oils are present with each, as separately packaged, respectively, of the oxidizing components and the alkaline booster components. In some embodiments the oils that are mixed with the oxidizing and alkaline booster components may be the same or may be different. In some examples, the percentage of oil mixed with the oxidizing and alkaline booster components may be the same or may be different. In one example, the oil phase is 20% mineral oil, and 40% dimethicone.

In accordance with the various embodiments, the composition provides a measurable brightening effect to keratinous tissue, whereby, when applied repeatedly over time to keratinous tissue the composition affects a change in skin brightness (luminosity) and skin radiance.

In accordance with some of the various embodiments, the fatty compound is an oxidation resistant fatty compound.

In accordance with the various embodiments, the composition provides a measurable radiance and glow effect to keratinous tissue, whereby, when applied repeatedly over time to keratinous tissue the composition affects a change in skin radiance and glow characterized by a radiance score from about 2.5 after one application to about 3.75 after applying it twice per week for 4 weeks.

Other features and advantages of the present invention will be apparent from the following more detailed description, taken in conjunction with the accompanying drawings which illustrate, by way of example, the principles of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

The term "alkaline booster" as used herein means compositions comprising at least one alkaline agent with a final pH >7, or a final pH >8. The alkaline agent may be organic or mineral or hybrid with a pKa at 25° C. greater than 7.5. One example of a composition that includes alkaline boosters is described in U.S. Pat. No. 7,927,381. The disclosed composition is intended for use on hair, and includes at least one fatty substance and at least one surfactant, at least one alkaline agent, at least one oxidizing agent, and in some embodiments at least one dye, wherein the composition includes one or more of ammonia and persulfate based alkaline boosters.

The terms "ammonia-free" and "persulfate-free" means that the composition comprises less than a trace amount, for example, less than 0.001% by weight of the composition, of an ammonia containing ingredient or a persulfate containing ingredient, and more particularly that the ingredient has not been intentionally added, but may be included as a by-product or carry-over of another ingredient. In some embodiments, each of ammonia-free and persulfate-free means that the composition is devoid, respectively, of ammonia and ammonia containing ingredients, and of persulfates, persulfate containing ingredients, perborates, alkali metal percarbonates, alkaline-earth metal percarbonates, peracids and precursors thereof.

The term "oxidation resistant" means and refers to a fatty compound, such as an oil, that is free of unsaturated functions, ester groups. The fatty compound can be chosen from C6-C16 lower alkanes, non-silicone oils of animal, plant, mineral or synthetic origin fatty alcohols, fatty acids, non-silicone waxes, and silicones.

"Cosmetically acceptable" means compatible with any keratinous substrate. For example, "cosmetically acceptable carrier" means a carrier that is compatible with any keratinous substrate.

"Skin-brightening" means and refers to improvement in radiance, glow effect and lightening effect to keratinous tissue.

Applicants have surprisingly discovered that a composition including ammonia-free and persulfate-free alkaline boosters, such as one or more of guanidine carbonate, arginine, monoethanolamine, triethanolamine, potassium hydroxide, sodium bicarbonate together with hydrogen peroxide, and at least one non-oxidizing fatty compound, present in an amount that is greater than or equal to 30% by weight, based on the weight of the composition, demonstrates skin-brightening efficacy without strong, unpleasant odor and provides a skin smoothing effect to impart a glow to the skin. The brightening efficacy increases with the number of application.

In some embodiments, a skin-brightening cosmetic composition comprises hydrogen peroxide, at least one alkaline booster, and at least one fatty compound. The skin-brightening cosmetic composition is ammonia-free and persulfate-free. The composition demonstrates efficiency in whitening that is at least the same as with ammonia containing compositions.

In some embodiments, a skin-brightening cosmetic composition comprises from about 1 to about 4 wt % of hydrogen peroxide; from about 1 to about 5 wt % of at least one alkaline booster selected from the group consisting of guanidine carbonate, arginine and combinations thereof; and from about 50 to about 60 wt % of at least one oxidation resistant fatty compound selected from the group consisting of mineral oil, hemisqualane, squalane, dimethicone and combinations thereof. The skin-brightening cosmetic composition is ammonia-free and persulfate-free. The composition demonstrates efficiency in whitening that is at least the same as with ammonia containing compositions.

Hydrogen Peroxide

The hydrogen peroxide in the cosmetic composition, according to the disclosure in some embodiments, is discovered to be compatible with cosmetic applications. In some embodiments, the composition may comprise PVP $H_2O_2$.

In accordance with the various embodiments, amount of hydrogen peroxide present in the composition can range from about 1% to about 10%, from about 1 to about 7%, from about 1.0 to about 5%, from about 1.0 to about 4.0%, from 1.5 to about 3.5%, from 2.0 to about 3.0% or any suitable combination, sub-combination, range, or sub-range thereof by weight, based on the weight of the composition. One of ordinary skill in the art, however, will appreciate that other ranges are within the scope of the invention.

Thus, hydrogen peroxide may be present, by weight, based on the total weight of the composition, from about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, to about 10 weight percent, including increments and ranges therein and there between.

Alkaline Booster

In accordance with the disclosure, one or more ammonia-free, persulfate-free alkaline booster is present in the composition. In some embodiments, the alkaline booster is selected from organic amines and salts, mineral based salts, alkali metal hydroxides, alkali earth metal hydroxides, alkali metal salts, and combinations thereof. In some embodiments, the alkaline booster is selected from guanidine carbonate, arginine, monoethanolamine, triethanolamine, potassium hydroxide, sodium bicarbonate and combinations thereof. In some embodiments the composition includes an optional catalyst. In some embodiments the optional catalyst is manganese dioxide. Although these alkaline boosters are given as an example, it will be appreciated that other alkaline boosters compatible with cosmetic applications known in the art may be used. Thus, the alkaline booster may be organic or mineral or hybrid with a pKa at 25° C. greater than 7.5. For example, lysine, carnosine, KOH, NaOH, and the like.

In accordance with the various embodiments, amount of alkaline booster present in the composition can range from about 1% to about 5%; from about 1.5 to about 4.5%, from about 2.0 to about 4.0%, from about 2.5 to about 3.5% or any suitable combination, sub-combination, range, or sub-range thereof by weight, based on the weight of the composition. In some embodiments according to the disclosure, the composition includes at least about 2% of the at least one alkaline booster. Thus, in some embodiments, the at least one alkaline booster is present in an amount that is not less than about 2%, based upon the total weight of the composition. One of ordinary skill in the art, however, will appreciate that other ranges are within the scope of the invention. In some embodiments, two or more alkaline boosters are present.

Thus, one or a combination of alkaline boosters may be present, by weight, based on the total weight of the composition, from about from about 1.0, 1.5, 2.0, 2.5, 3.0, 3.5, 4.0, 4.5, to about 5.0 weight percent, including increments and ranges therein and there between.

Fatty Compound

In accordance with the disclosure, one or more fatty compound or oil is present in the composition. The fatty compound includes one or more of non-silicone oils of animal, plant, animal or synthetic origin, fatty alcohols, fatty acids, esters of a fatty acid and/or of a fatty alcohol, non-silicone waxes, and silicones.

In some embodiments, the fatty compound includes, but is not limited to: 1) C6-C16 lower alkanes, non-silicone oils of animal, plant, animal or synthetic origin, fatty alcohols, fatty acids, non-silicone waxes, and silicones; 2) hydrocarbon-based oils of animal origin, such as perhydrosqualene; 3) fluoro oils, perfluoromethycyclopentane and perfluoro-1, 3-dimethylcyclohexane, sold under the name FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the same PF 5052® by the company 3M. 4) linear or branched saturated fatty alcohols having from 6 to 30 carbon atoms or from 8 to 30 carbon atoms, for instance cetyl alcohol, stearyl alcohol, and the mixture thereof (cetylstearyl alcohol), octyldodecanol, 2-butyloctanol, 2-hexyldecanol, 2-undecylpentadecanol, oleyl alcohol, and linoleyl alcohol.

In some embodiments, at least one fatty substance describes an organic compound that is insoluble in water at ordinary ambient temperature (25° C.) and at atmospheric pressure (760 mmHg). In some embodiments, the at least one fatty substance has a water solubility of less than 5%. In some embodiments, the at least one fatty substance has a water solubility of less than 1%. In some embodiments, the at least one fatty substance has a water solubility of less than 0.1%. Although these fatty compounds are given as an example, it will be appreciated that other compounds compatible with cosmetic applications known in the art may be used.

In accordance with the various embodiments, amount of fatty compound present in the composition can range from about 30% to about 80%, or from about 35 to about 60%, from about 40 to about 59%, from about 45 to about 58%, from about 50 to about 57%, from about 52 to about 56%, from about 30 to about 55%, from about 30 to about 60% or any suitable combination, sub-combination, range, or sub-range thereof by weight, based on the weight of the composition. In some embodiments according to the disclosure, the composition includes at least about 30% of the fatty compound. And, in some embodiments according to the disclosure, the composition includes at least about 50% of the fatty compound. Thus, in some embodiments, the fatty compound is present in an amount that is not less than about 30%, or not less than about 50%, based upon the total weight of the composition. One of ordinary skill in the art, however, will appreciate that other ranges are within the scope of the invention. In some embodiments, two or more fatty compounds are present. And, in some embodiments, one or more fatty compounds are present wherein at least one is an oxidation resistant fatty compound.

Thus, any one of or a combination of fatty compounds may be present, by weight, based on the total weight of the composition, from about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, to about 80 weight percent, including increments and ranges therein and there between.

Solvent

In accordance with the disclosure, one or more solvent is present in the composition. The solvent present in the cosmetic composition, according to the disclosure, includes, but is not limited to, water, alcohol, propylene glycol, or combinations thereof. Although these solvents are given as an example, it will be appreciated that other solvents compatible with cosmetic applications known in the art may be used.

In accordance with the various embodiments, solvent is present in a given composition in an amount of from about 1% to about 70%, or any suitable combination, sub-combination, range, or sub-range thereof by weight, based on the weight of the composition. One of ordinary skill in the art, however, will appreciate that other ranges are within the scope of the invention.

Thus, one or a combination of solvents may be present, by weight, based on the total weight of the composition from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, to about 70 weight percent, including increments and ranges therein and there between.

Water

The compositions comprise from about 1 to about 70% by weight of water, with respect to the total weight of the composition. In some embodiments, he amount of water in the composition can range from about 1 to about 50%, or any suitable combination, sub-combination, range, or sub-range thereof by weight, based on the weight of the composition.

The pH of the composition is not limited but is generally between 2 and 12, and in some embodiments is one of between 3 and 11, and between 5 and 9, and between 6 and 8, and 7. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid. More particularly the pH of Part A (hydrogen peroxide containing) part is adjusted by phosphoric acid; the pH of Part B (alkaline booster containing) is tuned by concentration of alkaline agents.

Thus, water may be present by weight, based on the total weight of the composition, from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, to about 70 weight percent, including increments and ranges therein and there between.

Surfactant

In some embodiments, the composition includes at least one surfactant. The at least one surfactant may be selected from nonionic surfactants and anionic surfactants. In some embodiments, the composition includes one, two, three or more surfactants. In some exemplary embodiments, the surfactant or surfactants are nonionic.

Exemplary anionic surfactants include, but are not limited to, the salts (in particular alkali metal salts, for example, sodium salts, amine salts such as aminoalcohol salts or alkaline-earth metal salts such as magnesium salts) of the following compounds: alkyl sulfates, alkyl ether sulfates, alkylamido ether sulfates, alkylaryl polyether sulfates, monoglyceride sulfates; alkylsulfonates, alkylamide sulfonates, alkylarylsulfonates, α-olefin sulfonates, paraffin sulfonates; alkyl phosphates, alkyl ether phosphates; alkylsulfosuccinates, alkyl ether sulfosuccinates, alkylamidesulfosuccinates; alkylsulfosuccinamates; alkylsulfoacetates; acylsarcosinates; acylisethionates and N-acyltaurates; salts of fatty acids such as oleic acid, ricinoleic acid, palmitic acid or stearic acid, coconut oil acid or hydrogenated coconut oil acid; alkyl-D-galactoside uronic acid salts; acyllactylates; salts of polyoxyalkylenated alkyl ether carboxylic acids, of polyoxyalkylenated alkylaryl ether carboxylic acids or of polyoxyalkylenated alkylamido ether carboxylic acids, in particular those having from 2 to 50 ethylene oxide groups; and mixtures thereof.

Exemplary nonionic surfactants include, but are not limited to, monooxyalkylenated or polyoxyalkylenated, monoglycerolated or polyglycerolated nonionic surfactants. The oxyalkylene units may be oxyethylene or oxypropylene units, or a combination thereof. In some embodiments, the oxyalkylene units are oxyethylene units. Exemplary oxyalkylenated nonionic surfactants include, but are not limited to: oxyalkylenated (C8-C24)alkylphenols, saturated or unsaturated, linear or branched, oxyalkylenated C8-C30 alcohols, saturated or unsaturated, linear or branched, oxyalkylenated C8-C30 amides, esters of saturated or unsaturated, linear or branched, C8-C30 acids and of polyethylene glycols, polyoxyethylenated esters of saturated or unsaturated, linear or branched, C8-C30 acids and of sorbitol, saturated or unsaturated, oxyethylenated plant oils, condensates of ethylene oxide and/or of propylene oxide, inter alia, alone or as a mixture.

In some embodiments, the at least one surfactant present in the composition is a nonionic surfactant. In some exemplary embodiments, one or more surfactants in the composition are selected from the group consisting of CETETH-2, DECYL GLUCOSIDE, STEARETH-2, STEARETH-20. In some exemplary embodiments a composition according to the disclosure includes two or more of non-ionic surfactants selected from the group consisting of CETETH-2, DECYL GLUCOSIDE, STEARETH-2, STEARETH-20.

In some embodiments, the at least one surfactant is present in the composition in an amount ranging from about 0.1% to about 15% by weight relative to the weight of the composition. In some embodiments, the at least one surfactant is present in the composition in an amount ranging from about 0.5% to about 3.5% by weight, based upon the total weight of the composition.

In some embodiments, one or more surfactants, alone or in combination, can be present in the composition according to the disclosure, and in some embodiments, each surfactant may be present from about 0.1% to about 5% by weight, from about 0.25% to about 2.5% by weight, from about 0.5% to about 1.8%, from about 0.5 to about 1.25%, and from about 0.5 to about 0.8%, or any suitable combination, sub-combination, range, or sub-range thereof by weight, based on the weight of the composition.

Thus, one or a combination of surfactants may be present, by weight, based on the total weight of the composition, from about 0.1, 0.2, 0.3, 0.4, 0.5, 0.6, 0.7, 0.8, 0.9, 1.0, 2, 3, 4, 5, 6, 7, 8, 9, 10, 11, 12, 13, 14, to about 15 weight percent, including increments and ranges therein and there between.

Polymer

In some embodiments, one or more other components, such as polymers can be present in the composition according to the disclosure from about 0.05% to about 50% by weight, from about 0.05% to about 15% by weight, from about 0.1 to about 2%, from about 0.25 to about 1.5%, and from about 0.25 to about 0.5%, or any suitable combination, sub-combination, range, or sub-range thereof by weight, based on the weight of the composition. In some exemplary embodiments, polymers are selected from cetyl hydroxyethyl cellulose, *Sclerotium* gum at 1% or more by weight, and combinations of these.

Thus, one or a combination of polymers may be present, by weight, based on the total weight of the composition, from about 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 weight percent, including increments and ranges therein and there between.

Chelating Agents

In some embodiments, one or more other components, such as chelating agents can be present in the composition according to the disclosure from about 0.01% to about 2% by weight, from about 0.02% to about 1.5% by weight, from about 0.02% to about 1%, from about 0.02% to about 0.5%, and from about 0.025 to about 0.15%, or any suitable combination, sub-combination, range, or sub-range thereof by weight, based on the weight of the composition. In some exemplary embodiments, chelating agents are selected from ethylenediaminetetraacetic acid (EDTA), tetrasodium etidronate, tetrasodium pyrophosphate, pentasodium ethylenediamine tetramethylene phosphonate, sodium staninate and combinations of these.

Thus, one or a combination of chelating agents may be present, by weight, based on the total weight of from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 up to about 2 weight percent, including increments and ranges therein and there between.

Optional Components

In some embodiments, there may be one or more actives present in the cosmetic composition, according to the disclosure, the additive selected from, for example, humectants, such as acetamide MEA, glycols, such as glycerin and propylene glycol; alcohol; anti-microbial components, salicylic acid, alpha hydroxy acid; including, phenolic compounds, such as chalcones, flavones, flavanones, flavanols, flavonols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, and phenolic terpenes, resveratrol, curcumin, pinoresinol, ferulic acid, hydroxytyrosol, cinnamic acid, caffeic acid, p-coumaric acid, baicalin (*Scutellaria baicalensis* root extract), pine bark extract (*Pinus pinaster* bark/bud extract), ellagic acid; and vitamins and vitamin derivatives, such as tocopherol and ascorbic acid; and combinations thereof.

In some embodiments, there may be one or more other components present in the cosmetic composition, according to the disclosure, the other components selected from, fillers such as clays, talc, organic thickeners with for instance, anionic, cationic, nonionic, and amphoteric polymeric associative thickeners and combinations thereof; penetrants; sequestrants; fragrances; dispersants; film-forming agents; ceramides; opacifiers and combinations thereof. Although the aforementioned optional components are given as an example, it will be appreciated that other optional components compatible with cosmetic applications known in the art may be used.

In accordance with the various embodiments, amount of actives and other components present in the composition can range from about 0 to about 50%, from about 0.5 to about 30%, from about 1.5 to about 20%, and from about 5 to about 15%, or any suitable combination, sub-combination, range, or sub-range thereof by weight, based on the weight of the composition.

In some embodiments, one or more actives, alone or in combination, can be present in the composition according to the disclosure from about 0.05 to about 50% by weight, from about 0.05% to about 2.5% by weight, from about 0.1 to about 2%, from about 0.25 to about 1.5%, and from about 0.5 to about 1.25%, or any suitable combination, sub-combination, range, or sub-range thereof by weight, based on the weight of the composition.

In some embodiments, one or more other components, such as preservatives, vitamins, preservatives, and the like, alone or in combination, can be present in the composition according to the disclosure from about 0.05 to about 50% by weight, from about 0.05% to about 25% by weight, from about 0.1 to about 10%, from about 0.25% to about 5%, and from about 0.5 to about 3.5%, or any suitable combination, sub-combination, range, or sub-range thereof by weight, based on the weight of the composition. In some exemplary embodiments, preservatives may include sodium salicylate, and vitamins may include ascorbic acid, tocopherol and combinations of these.

Thus, one or a combination of optional components may be present, by weight, based on the total weight of the composition, from about 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 weight percent, including increments and ranges therein and there between.

Articles of Manufacture

In accordance with the various embodiments, the composition may be provided in a kit or other article of manufacture, such as, a mask, cream, or lotion.

In one example, the article of manufacture may be a packet with separate packages or chambers separated by a frangible seal between the chambers. In use, the seal is broken by the user to contact the separately packaged sub compositions and mix them prior to application onto the skin.

In some other embodiments, the packaging is a single tube with a seal between the two components that is broken to mix. In other embodiments, the packaging can be a single container holding a suspension of encapsulated material that is mixed/broken to disperse and mix. And in yet other embodiments, the packaging is otherwise sufficient to retain the oxidizing material separate from the alkaline booster component until the composition is intended to be applied to keratinous tissue.

It will be appreciated that in the various embodiments of packaging, that the sub compositions that are packaged are maintained as separate until the composition is intended to be applied to keratinous tissue, at which time they are combined and mixed. Generally, the oxidizing material separate from the alkaline booster component until the composition is intended to be applied to keratinous tissue. Thus, one sub composition includes at least the hydrogen peroxide and any additional optional oxidizing agent, and one sub composition includes at least the alkaline booster. Variously, each of the sub compositions may include any one or more of the fatty compound and any one or more of solvents, surfactants, polymers, actives and other components. Further, any one or more of the fatty compound and any one or more of solvents, surfactants, polymers, actives and other components may be separately packaged from the other sub compositions, such that the article of manufacture may comprise more than two separate packages or package chambers.

In accordance with the various embodiments, a skin-brightening cosmetic composition is in a form including a suspension, lotion, cream, serum, essence, gel, stick, spray, ointment, paste, foam, mousse, cream, wipe, patch, strip, film-forming product, facial masks or skin masks.

EXAMPLES

Testing:

In Vitro Stratum Corneum and Hair Swatch Tests:

It is well known that some individuals tend to have more facial hair than others. For such consumers, it is desirable to have a brightening product that lightens the facial hair and skin in a similar level to avoid superficial, golden hair visible on face. Therefore, evaluation of inventive and comparative compositions was performed on both hair and stratum corneum.

In vitro stratum corneum tests were conducted as follows: three stratum corneum samples (pre-conditioned for 17 h at 75% relative humidity) were treated with compositions for an exposure period of 15 minutes with no external heat or occlusion. Following treatment, the samples were rinsed and dried. The color of the stratum corneum was measured before and after treatment, and the individual change of Luminosity L* before and after treatment on white background was calculated and reported as ΔL (change in luminosity).

In vitro hair swatch tests were conducted as follows: ~1 g hair swatch (natural level 6, 15 cm long) was treated with ~20 g composition mixture on a hot plate with a surface temperature ~27° C. After 15 minutes, the hair swatch was washed under warm running water to completely clean the hair swatch, followed by blow dry.

In Vivo Skin Tests:

In vivo clinical studies were conducted among dark skin tone population. Depending on the study design, compositions were applied on back or face, left on for 15 min and then rinsed off and air dried. Skin Brightness was determined using instrumental evaluation. Skin Brightness is related to luminosity and can be measured instrumentally by the change of luminosity ($\Delta L$). Skin radiance was evaluated by clinical scoring, which uses experts to rate the skin radiance based on rating scales. Skin radiance is a subjective concept based on the expert evaluator's perception, and usually relates to a combination of even tone (color), luminosity (contrast), imperfections (dark circles, spots) and firmness. The skin radiance level is evaluated by experts based on a 1-5 scale of clinical scoring.

Results:

Example 1: Results with In Vitro Hair and Stratum Corneum Change in Luminosity, Inventive Compositions and Compositions Comprising Ammonia Inventive composition is the Inventive Example 1 shown in Table 3, wherein Part A and Part B are combined in equal amounts just prior to application.

Comparative composition is the Comparative Example 1 shown in Table 4 (includes ammonium bicarbonate as booster).

TABLE 1

Lightening efficacy of compositions with and without ammonia in in vitro hair and stratum corneum test:

|  | Comparative Example 1 | | Inventive Example 1 | |
| --- | --- | --- | --- | --- |
|  | PART A | PART B | PART A | PART B |
| H2O2 | 7% | | 7% | |
| Guanidine Bicarbonate | | 4% | | 4% |
| Ammonium Bicarbonate | | 1.12% | | |
| oil | 50 | 60 | 50 | 60 |
|  | Fla 1 = Part A:Part B 1:1 pH = 9.0 ± 0.5 | | Fla 2 = Part A:Part B 1:1 pH = 9.0 ± 0.5 | |
| $\Delta L$ on hair swatch | 5.12 ± 0.21 | | 3.7 ± 0.16 | |
| $\Delta L$ on SC with brown background | 1.4 ± 0.2 | | 1.3 ± 0.5 | |

In vitro hair swatch test showed that the inventive composition lacking ammonia provides significantly decreased lightening efficacy as compared with the comparative composition, while both inventive and comparative provide comparable stratum corneum lightening efficacy. For purposes of skin lightening in at least a single application, the inventive composition is advantageous in that it lacks the strong and generally disagreeable features of unpleasant smell and skin sensitivity that are conferred by ammonia.

Example 2: In Vitro Stratum Corneum Change in Luminosity, Inventive Compositions with and without Oil and Over Multiple Applications Inventive composition is the Inventive Example 1 shown in Table 3 wherein Part A and Part B are combined in equal amounts just prior to application.

Comparative composition is the Comparative Example 2 shown in Table 4 (without oil).

In vitro stratum corneum tests were conducted with and without oil, and over one or multiple applications. Table 2 provides the results.

TABLE 2

In vitro SC test shows that the efficacy increases with the increased oil content and increased number of application:

|  | Comparative Example 2 (without oil) | | Inventive Example 1 | | Inventive Example 1 | | Inventive Example 1 | |
| --- | --- | --- | --- | --- | --- | --- | --- | --- |
|  | PART A | PART B | PART A | PART B | PART A | PART B | PART A | PART B |
| H2O2 | 7% | | 7% | | 7% | | 7% | |
| Guanidine Bicarbonate | | 4% | | 4% | | 4% | | 4% |
| oil | 0 | 0 | 50 | 60 | 50 | 60 | 50 | 60 |
|  | Fla 1 = Part A:Part B 1:1 | | Fla 2 = Part A:Part B 1:1 | | Fla 2 = Part A:Part B 1:1 | | Fla 2 = Part A:Part B 1:1 | |
|  | pH = 9.0 ± 0.5 | | pH = 9.0 ± 0.5 | | pH = 9.0 ± 0.5 | | pH = 9.0 ± 0.5 | |
| # of application on SC | 1 | | 1 | | 2 | | 3 | |
| $\Delta L$ on SC with brown background | 0.9 ± 0.4 | | 1.3 ± 0.5 | | 1.9 ± 0.7 | | 2.8 ± 0.5 | |

As shown in Table 2, the brightening efficacy of the inventive composition increases as the oil content increases from between about 0% to about 50%. According to the in vitro results, the lightening efficacy with the compositions including oil were significantly better than those without, and the lightening improved with repeated applications over time. As shown, the increase in lighting with the inventive compositions including oil after three applications is $\Delta L=2.8$ compared to $\Delta L=1.3$ after 1 application.

Example 3: In Vivo Stratum Corneum Change in Luminosity Over Multiple Applications, Comparing Inventive Composition with Hydroquinone Containing Composition Inventive composition is the Inventive Example 1 shown in Table 3 wherein Part A and Part B are combined in equal amounts just prior to application.

Comparative composition comprises hydroquinone.

In vivo tests were conducted as described above, with application of the compositions being made on the back of test subjects. The inventive compositions were applied twice weekly over four weeks; comparative compositions containing Hydroquinone at 2% were applied five times per week over four weeks, These results in vivo follow the same trend as the in vitro results, demonstrating that an increased change in brightness can be achieved, for example an increase in brightness of $\Delta L=1.3$ after two applications per week for 4 weeks using an inventive composition according to the disclosure as compared with a modest increase in brightness of only $\Delta L=0.3$ after the first application. The comparative showed a maximum $\Delta L=0.5$ after five applications per week for 4 weeks, and no increase in brightness after the initial application.

Example 4: In Vivo Stratum Corneum Change in Skin Brightness (Luminosity—Measured) and Radiance (Expert Scored)

Inventive composition is the Inventive Example 1 shown in Table 3 wherein Part A and Part B are combined in equal amounts just prior to application.

Comparative composition is the Comparative Example 1 shown in Table 4 (includes ammonium bicarbonate as booster).

The inventive composition provided a measurable radiance and glow effect to keratinous tissue, whereby, when applied repeatedly over time to keratinous tissue, the composition affected Skin Brightness (luminosity) characterized by an $\Delta L=1.6$ after the second application and a sustained $\Delta L=1.2$ after applying it twice per week for 4 weeks. The inventive composition affected Skin Radiance characterized by a radiance score from 2.6 after one application to 3.55 after applying it twice per week for 4 weeks, wherein the radiance score ranges from 1=dull, least radiant or bright to 5=most radiant or bright.

Inventive Compositions

TABLE 3

| | Inventive cosmetic compositions | | | | | |
| --- | --- | --- | --- | --- | --- | --- |
| | Inventive Example 1 | | | Inventive Example 2 | | |
| Type | PART A | PART B | FINAL (A + B, EQUAL PARTS) | PART A | PART B | FINAL (A + B, EQUAL PARTS) |
| BOOSTER (ARGININE) | 0 | 0 | 0 | 0 | 5 | 2.5 |
| BOOSTER (GUANIDINE CARBONATE) | 0 | 4 | 2 | 0 | 0 | 0 |
| HYDROGEN PEROXIDE | 7 | 0 | 3.5 | 7 | 0 | 3.5 |
| FATTY COMPOUND | 50 | 60 | 55 | 50 | 60 | 55 |
| NONIONIC SURFACTANTS | 3.5 | 3.5 | 3.5 | 2.25 | 2.25 | 2.25 |
| CHELATING AGENTS | 0.15 | 0.15 | 0.15 | 0.15 | 0.15 | 0.15 |
| VITAMINS | 0.2 | 0.2 | 0.2 | 0.2 | 0.2 | 0.2 |
| POLYMER | 0.75 | 0.75 | 0.75 | 0.75 | 0.75 | 0.75 |
| PRESERVATIVE | 0.02 | 0.02 | 0.02 | 0.02 | 0.02 | 0.02 |
| WATER | QS 100 | QS 100 | QS 100 | QS 100 | QS 100 | QS 100 |

Comparative Compositions

TABLE 4

| | Comparative cosmetic compositions | |
| --- | --- | --- |
| Type | Comparative Example 1 | Comparative Example 2 |
| BOOSTER (AMMONIUM BICARBONATE) | 2 | 0 |
| BOOSTER (GUANIDINE CARBONATE) | 0 | 2 |
| HYDROGEN PEROXIDE | 3.5 | 3.5 |
| FATTY COMPOUND | 55 | 0 |
| NONIONIC SURFACTANTS | 3.5 | 3.5 |
| CHELATING AGENTS | 0.15 | 0.15 |
| VITAMINS | 0.2 | 0.2 |
| POLYMER | 0.75 | 0.75 |
| PRESERVATIVE | 0.02 | 0.02 |
| WATER | QS 100 | QS 100 |

Raw Materials

Compositions and compositions as described in the representative embodiments herein are selected from commercially available materials, including, for example: hydrogen peroxide; mineral oil, hemisqualane, guanidine carbonate and arginine.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material of the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A skin-brightening cosmetic composition comprising:
   a. about 1% to about 10% by weight of hydrogen peroxide, based on the total weight of the composition;
   b. about 1% to about 5% by weight of at least one alkaline booster comprising at least guanidine carbonate, based on the total weight of the composition;
   c. about 30% to about 80% by weight of at least one fatty compound comprising a compound selected from the group consisting of mineral oil, hemisqualane, squalane, dimethicone and combinations thereof, based on the total weight of the composition; and
   d. a catalytic amount of manganese dioxide,
   wherein the skin-brightening cosmetic composition is dye-free, ammonia-free, and persulfate-free, and when applied to skin demonstrates skin brightening efficacy.

2. The composition of claim 1, wherein the composition is provided as a multi-part system comprising a plurality of parts, each of the parts in the plurality of parts separately including at least one sub-composition, a first part including a sub-composition comprising the hydrogen peroxide and a second part including a sub-composition comprising the at least one alkaline booster, wherein the at least one fatty compound component is included in at least one of the first and second sub-compositions and also included in a third sub-composition of a third part, wherein each of the plurality of parts discretely including the sub-compositions are combinable at the time of use.

3. The composition of claim 1, wherein the composition, when applied repeatedly over time to keratinous tissue, affects a change in skin brightness.

4. The composition of claim 1, wherein the hydrogen peroxide is employed in an amount of from about 1% to about 4% by weight, based on the total weight of the composition.

5. The composition of claim 1, wherein the at least one alkaline booster is employed in an amount of from about 1.5% to about 4.5% by weight, based on the total weight of the composition.

6. The composition of claim 1, wherein the at least one fatty compound is employed in an amount of from about 50% to about 60% by weight, based on the total weight of the composition.

7. The composition of claim 1, wherein the at least one alkaline booster further comprises at least one compound selected from the group consisting of arginine, monoethanolamine, triethanolamine, potassium hydroxide, sodium bicarbonate, and combinations thereof.

8. The composition of claim 1, wherein the at least one fatty compound further comprises a compound selected from the group consisting of liquid petroleum jelly, polydecenes, liquid esters of fatty acids, liquid esters of fatty alcohols, and mixtures thereof.

9. The composition of claim 1, wherein the composition further comprises a polymer selected from the group consisting of cetyl hydroxyethylcellulose, *Sclerotium* gum and combinations thereof.

10. The composition of claim 1, wherein the composition further comprises a preservative including sodium salicylate.

11. The composition of claim 1, wherein the composition further comprises a surfactant selected from the group consisting of steareth-2, steareth-20, ceteth-2, decyl glucoside and combinations thereof.

12. The composition of claim 1, wherein the composition further comprises a vitamin or vitamin derivative selected from the group consisting of ascorbic acid, tocopherol and combinations thereof.

13. The composition of claim 1, wherein the composition further comprises a solvent including water.

14. The composition of claim 1, wherein the composition further comprises a chelating agent selected from the group consisting of ethylenediaminetetraacetic acid (EDTA), tetrasodium etidronate, tetrasodium pyrophosphate, phosphoric acid and combinations thereof.

15. The composition of claim 1, wherein the composition is in a form selected from the group consisting of a suspension, cream, serum, essence, gel, toner, stick, spray, ointment, paste, foam, mousse, shaving cream, wipe, patch, strip, film-forming product, facial masks and skin masks.

16. A skin-brightening cosmetic composition comprising:
   a. from about 1% to 4% by weight, based on the total weight of the composition, of hydrogen peroxide;
   b. from about 1% to about 5% by weight, based on the total weight of the composition, of at least one alkaline booster selected from the group consisting of guanidine carbonate, arginine, monoethanolamine, triethanolamine, potassium hydroxide, sodium bicarbonate, and combinations thereof;
   c. from about 30% to about 60% by weight, based on the total weight of the composition, of at least one fatty compound selected from the group consisting of mineral oil, hemisqualane, and combinations thereof; and
   d. a catalytic amount of manganese dioxide,
   wherein the skin-brightening cosmetic composition is dye-free, ammonia-free, and persulfate-free.

17. The composition of claim 16 wherein the composition is provided as a multi-part system comprising a plurality of parts, each of the parts separately containing two or more sub-compositions each of which sub-compositions comprises one or a combination of the hydrogen peroxide, alkaline booster, and fatty compound, wherein the sub-compositions are combinable at the time of use.

18. The composition of claim 16, wherein the composition further comprises a polymer, a preservative, a surfactant, a vitamin, a vitamin derivative, a solvent, a chelating agent, or combinations thereof.

19. The composition of claim 16, wherein the at least one alkaline booster comprises at least guanidine carbonate, alone or combined with a compound that is selected from the group consisting of arginine, monoethanolamine, triethanolamine, potassium hydroxide, sodium bicarbonate, and combinations thereof.

20. A method for brightening skin, comprising applying to the skin a composition comprising:
   a. hydrogen peroxide, employed in an amount from about 1% to 4% by weight, based on the total weight of the composition;
   b. at least one alkaline booster including a compound selected from the group consisting of guanidine carbonate, arginine, monoethanolamine, triethanolamine, potassium hydroxide, sodium bicarbonate, and combinations thereof, employed in an amount from about 1% to about 5% by weight, based on the total weight of the composition;
   c. at least one fatty compound present from about 30% to about 80% by weight, based on the total weight of the composition, comprising a compound selected from the group consisting of mineral oil, hemisqualane, squalane, dimethicone and combinations thereof; and
   d. a catalytic amount of manganese dioxide,
   wherein the skin-brightening cosmetic composition is dye-free, ammonia-free, and persulfate-free, and wherein the composition is provided as a multi-part system, each of the parts of the multi-part separately containing two or more sub-compositions each of which two or more sub-compositions comprises one or a combination of the hydrogen peroxide, alkaline booster, and fatty compound components, which sub-compositions are combinable at the time of use.

21. The method of claim 20, wherein the hydrogen peroxide is employed in an amount of about 3.5% by weight, based on the total weight of the composition.

22. The method of claim 20, wherein the at least one alkaline booster is employed in an amount of from about 1.5% to about 4.5% by weight, based on the total weight of the composition.

23. The method of claim 20, wherein the at least one alkaline booster comprises at least guanidine carbonate, alone or combined with a compound selected from the group consisting of arginine, monoethanolamine, triethanolamine, potassium hydroxide, sodium bicarbonate, and combinations thereof.

24. The method of claim 20, wherein the at least one fatty compound is employed in an amount of from about 50% to about 60% by weight, based on the total weight of the composition.

25. The method of claim 20, wherein the composition further comprises a polymer, a preservative, a surfactant, a vitamin, a vitamin derivative, a solvent, a chelating agent, or combinations thereof.

26. A skin brightening kit for providing a skin brightening composition, the kit comprising: at least a first sub-composition and a second sub-composition, each of which are separately contained and are mixable prior to application to keratinous tissue to form the brightening composition, the brightening composition comprising:
   about 1% to about 10% by weight of hydrogen peroxide, based on the total weight of the skin brightening composition;

about 1% to about 5% by weight of at least one alkaline booster comprising at least guanidine carbonate, based on the total weight of the skin brightening composition;

about 30% to about 80% by weight of at least one fatty compound comprising a compound selected from the group consisting of mineral oil, hemisqualane, squalane, dimethicone and combinations thereof, based on the total weight of the skin brightening composition; and a catalytic amount of manganese dioxide, wherein the skin-brightening composition is dye-free, ammonia-free, and persulfate-free, a. the first sub-composition comprising the hydrogen peroxide and any additional optional oxidizing agent, and b. the second sub-composition comprising the alkaline booster, wherein either one or both of the first and second sub-composition comprises the at least one fatty compound, and wherein either one or both of the first and second sub-composition further comprises solvents, surfactants, polymers, actives, or combinations thereof.

27. The kit of claim 26, further comprising solvents, surfactants, polymers, actives, or combinations thereof in one or more additional sub-composition separately packaged from the first and second sub-compositions.

28. The kit of claim 26, wherein the at least one alkaline booster further comprises at least one compound selected from the group consisting of arginine, monoethanolamine, triethanolamine, potassium hydroxide, sodium bicarbonate, and combinations thereof.

* * * * *